United States Patent [19]

Blount

[11] Patent Number: 5,563,285

[45] Date of Patent: Oct. 8, 1996

[54] PRODUCTION OF SILICON-PHOSPHORUS CONTAINING COMPOSITIONS

[76] Inventor: David H. Blount, 6728 Del Cerro Blvd., San Diego, Calif. 92120

[21] Appl. No.: 160,176

[22] Filed: Dec. 2, 1993

[51] Int. Cl.$^6$ .................................................. C07F 7/08
[52] U.S. Cl. .............................. 556/404; 423/30; 528/25; 528/28; 528/29
[58] Field of Search ............................. 556/404; 423/30; 528/25, 28, 29

[56] References Cited

U.S. PATENT DOCUMENTS

| | | | |
|---|---|---|---|
| 4,389,530 | 6/1983 | Arit et al. | 556/404 |
| 4,523,009 | 6/1985 | Neilson et al. | 556/404 X |
| 5,082,958 | 1/1992 | Wright et al. | 556/404 X |

*Primary Examiner*—Paul F. Shaver

[57] ABSTRACT

A mixture of silicon and phosphorus are reacted with halides to produce silicon tetra halide, silicon-phosphorus halides and phosphorus trihalide composition. This composition is reacted with any suitable organic or inorganic-organic compound which has an active hydrogen, halide and/or a metal radical to produce organic silicon-phosphorus halides compositions which will react with inorganic, inorganic-organic and organic compound to produce an organic silicon-phosphorus product. These products may be used as flame-retardants, hydraulic fluid, building components, coating agents, adhesives and many other uses.

2 Claims, No Drawings

PRODUCTION OF SILICON-PHOSPHORUS CONTAINING COMPOSITIONS

The invention concerns compositions containing silicon and phosphorus atoms and their preparation and use. These compounds may contain a plurality of silicon atoms or a plurality of phosphorus atoms. They may be used as flame-retardants, hydraulic fluid, in production of compounds, polymers and many other uses.

BACKGROUND

The production of silicone compounds and organic phosphorus containing compounds are well known in the arts. The utilization of silicon-phosphorus and halide reaction products to produce novel silicon-phosphorus halide compounds and novel organic silicon-phosphorus compositions, polymers and products is new. These compounds, polymers and products have many uses such as reactants to produce novel compound and plastics, as a flame-retardant in plastics, as a lubricant, hydraulic fluid, adhesive, coating agent, rust inhibitor, building material, insulation, sound proofing and many other uses.

The object of this invention is to provide silicon-phosphorus halide compositions which are utilized to produce silicon-phosphorus halides, organic silicon-phosphorus compounds, polymers and products.

SUMMARY

The invention comprises silicon-phosphorus halides reaction compositions and their reaction products with organic and/or inorganic compounds. Another aspect of the invention is a process to produce silicon and phosphorus halide reaction compound; and the process to react these compounds with organic and/or inorganic compounds to produce organic silicon-phosphorus halides and organic silicon-phosphorus compositions which utilizes the following components:

(A) silicon compound;

(B) phosphorus compound;

(C) halide compound.

Components A, B and C are reacted to produce silicon-phosphorus halide compounds which is then reacted with (D) optionally, an organic compound;

(E) optionally, a basic salt forming compound (F) optionally, water;

to produce organic silicon-phosphorus halide compounds and/or an organic silicon-phosphorus product. The sequence of the addition of the Components A, B, C, D, E and F may be greatly varied depending on the end product desired. In the production silicon and phosphorus halide reaction compounds, the halide may be reacted separately with the silicon compound, and separately with the phosphorus compound then the silicon halide reaction compounds, are mixed with the phosphorus halide reaction compounds then reacted with an organic compound to produce an organic silicon-phosphorus halide composition, which is then reacted with more organic and/or inorganic compounds to produce organic silicon-phosphorus products.

In another process the silicon compound may be mixed with the phosphorus compound, then reacted with a halide compound to produce a composition of silicon halides, phosphorus halides and silicon-phosphorus halide compounds which are then reacted with an organic compound. In another method the halide compound is reacted with an organic compound, and then reacted with a mixture of silicon and phosphorus compounds to produce an organic-silicon-phosphorus halide composition and/or organic silicon-phosphorus products. In another method the organic compound may be reacted with a halide, to produce an organic halide which is then reacted with a metal compound (Grignard reagent), then reacted with the mixture of silicon halides, phosphorus halides and silicon-phosphorus halides to produce organic silicon-phosphorus halides or organic silicon-phosphorus products. In another method component E, a metal, may be reacted with an organic compound, to produce a metal compound which is then reacted with the reaction product of components A, B and C to produce an organic silicon-phosphorus halide and/or an organic silicon-phosphorus composition.

The organic silicon-phosphorus halide composition may be reacted with water or another organic compound or a metal organic compound or a Grignard reagent to produce organic silicon-phosphorus compositions. In another method, an organic tri or dichlorosilane may be mixed with phosphorus halide and an organic compound to produce an organic silicon-phosphorus composition.

Preferably, the phosphorus compound and silicon compound are mixed then reacted with a halide to produce a mixture of silicon halides, phosphorus halides and silicon-phosphorus halides which are then reacted with an organic compound. Another very suitable method is to react the halide with the silicon and phosphorus compounds separately then mix the two together, and then react the mixture with organic compounds.

The silicon tetrahalide, phosphorus trihalide and silicon-phosphorus halide composition may also be produced by mixing powder silica, phosphorus and carbon or a metal such as magnesium, then heating the mixture to a high enough temperature in an electric furnace to where the carbon combines with the oxygen and a mixture of silicon phosphorus, phosphorus and silicon is produced, then an excess of halogen is passed thru the hot mixture thereby producing a composition containing silicon tetrahalide, silicon-phosphorus halides, phosphorus trihalide and phosphorus pentahalide. The phosphorus is commercially produced from a mixture of calcium, phosphate, silica and carbon, by heating the mixture. Phosphorus is recovered by distillation.

The phosphorus trihalide, silicon-phosphorus halide and silicon tetrahalide composition may be modified by the addition of water in the amount of 1–2 mols to one mol of phosphorus trihalide to produce a silicon-phosphorus oxyhalides composition. This mixture may also be modified by the addition of phosphorus pentaoxide in the amount of about 1 to 2 mol of phosphorus pentaoxide to 6 mols of phosphorus trihalide thereby producing a silicon-phosphorus oxyhalides composition.

Component A

Any suitable silicon compound may be utilized in this invention such as silicon and silicon dioxide. Silicon is the preferred compound in production of silicon tetrachloride. Organic silicon halides and silicon halides may also be utilized. The organic silicon halide, preferably should contain at least 2 halogen radicals but preferably 3 halogen radicals. Examplificative silicon-halides include, but are not limited to the following compounds; silicon tetrachloride, silicon tetrabromide, silicon tetrafluoride, silicon tetraiodide, alkyl trichlorosilane, dialkyl dichlorosilane, aryl trichlorosilane, etc.

Component B

Any suitable phosphorus compound may be utilized in this invention such as phosphorus and phosphorus pentaoxide. Phosphorus is the preferred compound. The phosphorus oxide may be utilized to react with the phosphorus halides or silicon halides. Phosphorus halides such as phosphorus trichloride, phosphorus pentachloride, phosphorus tribomide, phosphorus pentachloride, phosphorus tribromide, phosphorus pentabromide, phosphorus trifluoride, phosphorus pentafluoride, phosphorus triiodide, phosphorus oxyhalides and mixtures thereof may be utilized. Phosphorus trichloride is the preferred phosphorus trihalide, and phosphorus oxychloride is the preferred phosphorus oxyhalide.

Component C

Any suitable halide compound may be utilized in this invention such as chlorine, fluorine, bromide and iodine and mixtures thereof. Chlorine is the preferred halide compound. Carbonyl chloride (phosgene) may also be used. Hydrogen halides such as hydrogen chloride, hydrogen fluoride and hydrogen bromide may also be utilized.

Compound D

Any suitable organic compounds may be utilized in this invention. Any organic compound that will react with a phosphorus or silicon radical may be utilized in this invention. Suitable organic compounds may be substituted, saturated or unsaturated or mixture thereof. Suitable compounds are organic and inorganic-organic compounds with one or more active hydrogen and/or halide and/or metal radicals. These compounds may be aliphatic, aromatic, aliphatic-aromatic, heterocyclic, inorganic-organic and mixtures thereof, and may be substituted, saturated and/or unsaturated. Suitable organic compounds include, but are not limited to alcohols, polyalcohols, epoxides, polyepoxides, organic acids and anhydrides, polycarboxyl acids and anhydrides, isocyanates, polyisocyanates, thioalcohols, thiophenols, aldehydes, halogenated alcohols and polyalcohols, epihalohydrins, halogenated organic acids and polycarboxyl acids, sulphonic acid chlorides, organic esters, ethers, thioethers, halomethyl compounds, ketones, nitriles, sulphonic acids, amines, polyamines, alkyl magnesium chloride, alkanes, alkenes, alkynes, alkyl halides, organometallic compounds, aryalkanes, arylalkenes, organic polyenes, aminophenols, proteins, terpenes, oils, fats, amides, polyamides, nitroalkanes, organic phosphates, phosphites, phosphonates and phosphines; carbohydrates, lignin, cellulose, amino acids, aromatic hydrocarbons, aromatic nitro compounds, arylalkenes, halogenated alkenes, aminoalcohols, etc. and mixtures thereof.

Any suitable organic compound containing the following radicals and mixtures thereof may be utilized in this invention:

—SH, —CH$_2$CL, —CH$_2$Br, —CH$_2$I, —CN, —NO$_2$, —COCl,

—COBr, —SO$_2$Cl, —SO$_2$Cl, —COOH, —S$_2$OH, —COO,

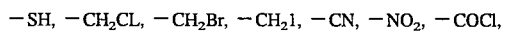

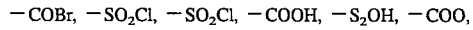

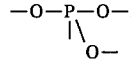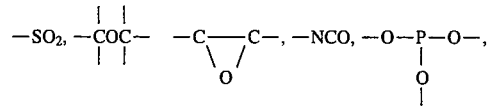

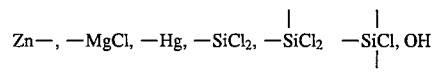

wherein R is an organic group.

A more detailed list of suitable organic compounds may be found in "Textbook of Organic Chemistry" by Carl R. Noller, published by W. B. Saunders Co., 1966, Philadelphia and London, and is incorporated herein by reference.

Component E

Any suitable basic salt forming compound may be utilized on this invention. Suitable compounds include, but are not limited to compounds containing alkali metals, alkaline earth metals, metals and ammonia radicals; amines, amino compounds, polyamines, aminoplasts, and mixtures thereof. Basic slat forming compound may be in the form of metals, oxides, hydroxides, carbonates, bicarbonates, salts of organic acids, silicates, natural minerals, sulfur, alkali polysulfides, etc., and mixtures thereof.

Component F

Water may be utilized to react with the silicon tetrahalide and phosphorus trihalide mixtures to produce silicon phosphorus oxyhalides. Water may also be utilized to react with the organic silicon-phosphorus halide to produce organic silicon-phosphorus compositions. Water may be used in the amount of one mol per mol of halide present in the silicon tetrahalide and phosphorus trihalide mixture or with the organic silicon-phosphorus halide compositions. An excess of water may be utilized if desired.

DETAILED DESCRIPTION OF THE INVENTION

The mixture of the components of this invention may take place in any suitable physical condition. Ambient pressure is usually satisfactory except when a gas compound is used, then it may be necessary to compress the gas until it is in the form of a liquid. In reacting the halides with silicon and phosphorus an elevated temperature is usually necessary. Silicon will react with dry chlorine at about 200°–300° C. and phosphorus will react with chlorine when in a molting stage. Temperatures up to 700° is required for phosgene to react with silicon to form silicon tetrachloride. The temperature may range from ambient temperature to 800° C. In some reactions to produce organic silicon-phosphorus halides compositions and organic silicon-phosphorus compositions it is necessary to cool the reaction mixture and in others it is necessary to use elevated temperature.

When a mixture of silicon and phosphorus is being reacted with a halide it is preferable for the silicon and phosphorus to be in a powdered form and heated to between the molting and boiling temperature of phosphorus, then dry halide gas is passed thru the hot powder. An excess of halides may be use, but at least 4 mols of halide for each mol of phosphorus should be used. Elevated temperature may be needed when an organic compound is reacted with the mixture of silicon halide, phosphorus halide and silicon-phosphorus halides and also when the organic silicon-phosphorus halides composition are reacted with other organic compounds but most of the reactions are exothermic.

In general, the liquid silicon-phosphorus halides, silicon halide and phosphorus halide mixture, produced form a mixture of silicon, phosphorus and halides contains about 7 mols of halide for 1 mol of silicon and one mol of phosphorus; whereby the valences available for further bonding is 7. There is some bonding between the silicon and phosphorus atoms which reduces the valences available for further bonding but the mixture may also contain phosphorus pentahalide. Bridging of the silicon moiety with the phosphorus moiety is represented by the corresponding hyphen in the compound nomenclature.

Any suitable amount of silicon compound may be mixed with phosphorus compound depending on the type of compounds desired. The amount of silicon may range from 1 part by weight to 100 parts by weight whereas the amount of phosphorus may range from 1 to 100 parts by weight. An excess of halides are used to pass thru the powdered mixture of silicon and phosphorus. When hydrogen chloride is utilized to react with silicon then 3 or 4 mols of hydrogen chloride are utilized for each mol of silicon to produce hydrogen silicon chlorides, hydrogen and silicon tetrachloride. The amount of halides needed depends on the ratio of silicon to phosphorus.

The ratio of organic compounds to that of the mixture of silicon halides, phosphorus halides and silicon-phosphorus halides may greatly depend on the composition or product desired. In the production of organic silicon-phosphorus halides composition the amount of organic compound utilized would depend on the amount of halide radical that was to be left on the organic silicon-phosphorus compound; in general one mol of the organic compound would be used for each halide atom present on the silicon-phosphorus halides, silicon halides and phosphorus halides molecules. In the production of organic silicon-phosphorus products sufficient organic molecules are utilized to equal the atoms of halides present on the organic silicon-phosphorus halides compound. Suitable amount of organic compound may range from up to 300 parts by weight.

A basic salt forming compound may be utilized to react with an organic compound to form an organic metal compound or an organic magnesium halide (Grignard reagent), and utilized to react with the silicon tetrahalide silicon-phosphorus halide and phosphorus trihalides mixture to produce organic silicon-phosphorus products. One mol of the Grignard reagent will react with one halide radical present in the organic silicon-phosphorus halide molecule.

In the production of polyurethane by the process of this invention, polyurethane and polyisocyanate catalyst and foam regulators may be utilized along with blowing agents. Flame retardants may be utilized in the production of plastic and foam product produced by this process. Free radical initiators along with their initiators may be utilized when needed in the polymerization of unsaturated compounds.

The organic silicon-phosphorus product of this invention may be further reacted with inorganic or organic compounds. When unsaturated radicals are present they may be reacted with other unsaturated organic radical by use of heat, ultra violet light or free radical initiators to form polymers. When the organic silicon-phosphorus products have one or more active hydrogens, halides or metal radicals it may be further reacted with compounds such as isocyanate, polyisocyanates, epoxides, polyepoxides, organic metal compounds, organic acid halides, polycarbolic acids, polycarboxylic anhydrides, etc.

The organic silicon-halides composition may be reacted with water to produce organic silicon-phosphorus polymer products. The water may be added in the amount of one mol of water to one mol of halide radical present at one time, then after the reaction is complete another mol is added until all the halide radicals have reacted with water to produce hydrogen halide. An excess of water may also be added at one time. The method used depends on the products desired.

The exact formula for the compounds and products produced in this invention is not known but there is a mixture of compounds produced when the halides react with a mixture of the silicon compounds and phosphorus compounds. The liquid mixture contains silicon halides, phosphorus halides (tri and penta halides) and silicon-phosphorus halides. This mixture contains compounds of the general formulae of:

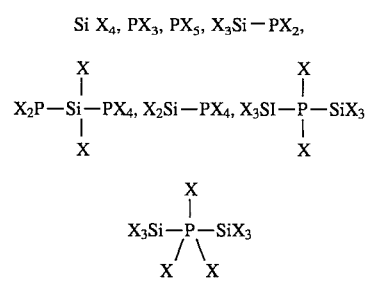

and other formulae depending on the ratio of Si to P. X is a halogen atom selected from the group consisting of chlorine, fluorine, bromide and iodine.

The silicon-phosphorus halide may also be produced by mixing powdered silicon dioxide, phosphorus oxides and carbon in a closed vessel which is vented. The mixture is heated until the carbon reacts with the oxygen in the silicon dioxide and phosphorus oxides to form CO thereby producing a silicon-phosphorus composition, then a dry gaseous halide is passed thru the hot silicon-phosphorus composition until a silicon-phosphorus halide composition is produced.

The ratio of the essential reactants and optional reactants with lead to the production of silicon-phosphorus containing compound and compositions of this invention may vary broadly speaking, with ranges as follows:

A. 1 to 100 parts by weight of silicon compound;

B. 1 to 100 parts by weight of phosphorus compound;

C. 4 mols or more of halide for each mol of Si and 3 to 5 mols of halide for each mol of P; an excess of halide may be utilized;

D. up to 300 parts by weight of organic compound;

E. up to 100 parts by weight of a basic salt forming compound;

F. up to 200 parts by weight of water.

DESCRIPTION OF PREFERRED EMBODIMENTS

The following examples which describe certain preferred embodiments of the processes may, of course, be varied as described above with similar results. Parts and percentages are by weight unless otherwise indicated.

EXAMPLE 1

Preparation of a silicon halide, silicon-phosphorus halide and phosphorus halides compositions:

A. About equal parts by weight of powdered silicon and phosphorus are mixed, then the mixture is heated until the phosphorus is melted, then heated to just below the phosphorus boiling point, in a closed vessel; then dry chlorine is passed over the hot silicon and phosphorus mixture until a mixture of silicon tetrachloride, phosphorus trichloride and silicon-phosphorus chlorides is produced. At least 7 mols of chlorine are added to 1 mol of silicon and 1 mol of phosphorus, B. About equal parts by weight of silicon tetrachloride and phosphorus trichloride are mixed, C. About equal parts by weight of silicon tetrachloride and phosphorus oxytrichloride are mixed, D. Example 1A is modified wherein two parts by weight of silicon is mixed with 1 part by weight of phosphorus, E. Example 1A is modified wherein one part by weight of silicon is mixed with 2 parts by weight of phosphorus.

EXAMPLE 2

About 50 parts by weight of methanol is added to a flask and then placed in an ice water both; then 20 parts by weight of the silicon tetrachloride, phosphorus trichloride and silicon-phosphorus chloride liquid mixture of 1A is slowly added to the methanol while agitating and hydrochloric acid evolve. The excess methanol is evaporated off of the liquid organic silicon-phosphorus composition.

EXAMPLE 3

Example 2 is modified wherein about 1 mol of methanol is used with 3 mols of the chlorine present on the silicon tetrachloride, phosphorus trichloride and silicon-phosphorus chlorides mixture thereby producing a liquid organic silicon-phosphorus chloride containing composition.

EXAMPLE 4

Example 2 is modified wherein the silicon tetrachloride and phosphorus trichloride mixture 1B is used in place of 1A mixture.

EXAMPLE 5

Example 2 is modified wherein the silicon tetrachloride and phosphorus oxytrichloride mixture of 1C is used in place of 1A.

EXAMPLE 6

Example 2 is modified wherein the silicon tetrachloride, phosphorus trichloride and silicon-phosphorus chlorides of 1D is used in place of 1A.

EXAMPLE 7

Example 2 is modified wherein the silicon tetrachloride, phosphorus trichloride and silicon-phosphorus chloride of 1E is used in place of 1A.

EXAMPLE 8

Example 2 is modified wherein another alcohol is used in place of methanol and is selected from the list below:
a) ethanol
b) 1-propanol
c) 1-butanol
d) pentanol
e) 2-propanol
f) 2-methyl-1-propanol
g) chlorhydrin
h) allyl alcohol
i) mixtures of the above.

EXAMPLE 9

Example 2 is modified wherein a polyhydroxy compound is used in place of methanol and is selected from the list below:
a) ethylene glycol
b) propylene glycol
c) 1,4-butanediol
d) glycerol
e) 1,2,3-propanetriol
f) 1,2,4-butanetriol
g) polypropylene glycol, mol. wt. 400
h) 1,2,10-decanetriol
i) mixtures of the above.

EXAMPLE 10

Example 2 is modified wherein an epoxide is used in place of methanol and selected from the list below:
a) propylene oxide
b) epichlorohydrin
c) epibromohydrin
d) ethylene oxide, added under pressure
e) 1,2-epoxybutane
f) 1,2-epoxydecane
g) allyl glycidyl ether
h) epifluorohydrin
i) 7,8-epoxy-2-methyloctadecane
j) epoxy-3 phenoxypropane
k) ethylene glycol diglycidyl ether
l) polyepoxy resin
m) mixtures of the above.

EXAMPLE 11

Example 2 is modified wherein sufficient methanol is added to the 1A mixture to produce organic silicon-phosphorus chlorides composition with at least two chloride radicals on each molecule, then mixed with acetylene in present of a platinum catalyst to produce an unsaturated organic silicon-phosphorus polymer, which is mixed with a catalytic amount of a free radical initiator with its initiators, benzoyl peroxide, thereby producing an organic silicon-phosphorus polymer product.

EXAMPLE 12

Example 11 is modified wherein another unsaturated organic compound and a free radical initiator are utilized in place of acetylene and selected from the list below:
a) acrylic acid
b) methyl acrylic acid
c) ethyl acrylic acid
d) acrylonitrile
e) allyl alcohol
f) unsaturated polyester resins
g) isoprene
h) chloroprene i) butadiene
j) vinyl acetate
k) acrolein
l) ethyl acrylic acid
m) allyl alcohol
n) propargyl alcohol
o) linseed oil
p) mixtures of the above.

EXAMPLE 13

Example 2 is modified wherein about equal parts by weight of an epoxy resin are mixed with the organic silicon-phosphorus composition to produce a solid resin.

EXAMPLE 14

About 10 parts by weight of 1B mixture, 10 parts by weight of propylene triol are slowly mixed in a cooled container and reacted for about 30 minutes then 10 parts by weight of propylene oxide are slowly added while agitating thereby producing an organic silicon-phosphorus composition with free hydroxyl groups.

EXAMPLE 15

Example 14 is modified wherein the reactants are mixed in methylene chloride and propylene oxide is replaced with another epoxide selected from the list below:
a) ethylene oxide
b) epichlorohydrin
c) epibromohydrin
d) epoxy-3 phenyl propane
e) epifluorohydrin
f) 1,2-epoxybutane
g) 1,2-epoxydecane
h) allyl glycidyl ether
i) polyepoxy resin
j) mixtures of the above.

EXAMPLE 16

Example 2 is modified wherein mixture 1B is used in place of mixture 1A and an organic compound selected from the list below is used in place of methanol:
a) acetic acid
b) acrylic acid
c) propionic acid
d) formaldehyde
e) acetoaldehyde
f) acetone
g) methanamide
h) propyl amine
i) methyl mercaptor
j) diethylene triamine
k) urea
l) dicyandiamide
m) melamine
n) thiourea
o) carbon disulfide
p) cellulose
q) alginic acid
r) phenol
s) aniline
t) tolylene diamine
u) tolylene diisocyanate
v) dimethyl hydrogen phosphite
w) phthalic acid
x) 3-methylfuran
y) furfural
z) furfuryl alcohol
and/or mixtures of the above.

EXAMPLE 17

Example 2 is modified wherein mixture 1C is used in place of mixture 1A and an organic compound selected from the list below is used in place of methanol:
a) allyl alcohol
b) benzaldehyde
c) polyvinyl alcohol
d) acrolein
e) creosote
f) castor oil
g) propane diamine
h) triethylamine
i) N-vinyl-2-pyrrolidone
j) tributoxyethyl phosphate
k) isobutyl vinyl ether
l) benzoic acid
m) aminobenzoic acid
n) sulfamic acid
o) ascorbic acid
p) potassium oxalate
q) succinic anhydride
r) fumaric acid
s) caprolactom
t) diethyl glycol
u) lead acetate
v) ammonium thiocyanate
w) methyl magnesium chloride
x) zinc
y) dimethyl mercury
z) mixtures of the above.

EXAMPLE 18

About 5 parts by weight of silicon tetrachloride, 5 parts by weight of phosphorus trichloride, 30 parts by weight of propylene oxide and 30 parts by weight of phthalic anhydride are slowly added and mixed in a flask, which is in an ice bath to keep the mixture cool. Hydrogen chloride evolves from the mixture then after about 2–4 hours the mixture is heated to just below the boiling point of the components for 1 to 4 hours thereby producing a solid polyester silicon-phosphorus product. These products may be used as molding material, coating agent, etc.

EXAMPLE 19

Example 18 is modified wherein the phthalic anhydride is added after the silicon tetrachloride, phosphorus trichloride and propylene oxide has reacted.

EXAMPLE 20

Example 18 is modified wherein another polycarboxylic acid anhydride and/or acid is utilized in place of phthalic anhydride and selected from the list below:
a) phthalic acid
b) linoleic acid
c) maleic acid
d) maleic anhydride
e) fumaric acid
f) succinic acid
g) adipic acid
h) azelaic acid
i) sebacic acid
j) mixtures of the above.

EXAMPLE 21

About 5 parts by weight of silicon tetrachloride, 5 parts by weight of phosphorus trichloride, 5 parts by weight of glycerol and 30 parts by weight of propylene oxide are slowly added while agitating to a flask, which is cooled by an ice water bath. Hydrogen chloride evolves from the flask. The mixture is allowed to react for 12 to 24 hours, then sodium silicate is added until the PH is about 7. Then 45 parts by weight of polymeric MDI (PAPI 27 by DOW), 0.5 parts by weight of dimethyl ethyl amine, 0.2 parts by weight of tin oxalate, 0.5 parts by weight of a silicon foam regulator (L6202 by Union Carbide) are added, mixed and reacted thereby producing a flame retardant foamed product.

EXAMPLE 22

Example 21 is modified wherein another polyisocyante is used in place of polymeric MDI and selected from the list below:
a) tolylene-2,4-diisocyanate
b) tolylene-2,6-diisocyanate
c) polymethylene polyphenyl isocyanate
d) diphenyl methane 4,4-diisocyanate
e) 3-methyl diphenyl-methane-4,4'-diicyanate
f) crude MDI
g) modified polyisocyanate (Mondur PF by Mobay)
h) mixtures of the above.

These flame retardant foamed products may be utilized for insulating, sound proofing, construction material, etc.

EXAMPLE 23

About 5 parts by weight of the silicon tetrachloride, phosphorus trichloride and silicon-phosphorus chloride of Example A1 and 20 parts by weight of caprolactam are slowly added and mixed in a cooled flask. Hydrogen chloride evolves from the flask. After 6–8 hours the mixture is heated to just below the boiling point of the mixture for 1 to 4 hours thereby producing a solid polyamide silicon-phosphorus product.

EXAMPLE 24

Example 23 is modified wherein 10 parts by weight of adipic acid with 10 parts by weight of hexamethylene diamine is utilized in place of caprolactum.

EXAMPLE 25

5 parts by weight of Example A1 and 20 parts by weight of propylene diamine are slowly mixed in a cooled container, hydrogen chloride evolves from the container. The mixture is allowed to react for 6–8 hours then mixed with equal weight of a polyepoxy resin (bisphenol-A-epichlorohydrin) thereby producing a solid flame-retardant epoxy silicon-phosphorus product. This product may be used as a coating agent, adhesive, cavity filler, etc.

EXAMPLE 26

About 20 parts by weight of the phenol silicon-phosphorus compound of Example 16R and 10 parts by weight of aqueous formaldehyde are heated while agitating at a temperature just below the boiling temperature of the components for 2–4 hours thereby producing a solid phenoplast silicon-phosphorus product.

EXAMPLE 27

Example 26 is modified wherein an amino silicon-phosphorus composition, selected from the list below is used in place of 16R thereby producing an amino silicon-phosphorus composition:
a) 16 k
b) 16 l
c) 16 m
d) 16 n

EXAMPLE 28

Example 26 is modified wherein another aldehyde is used in place of formaldehyde and selected from the group below:
a) acetoaldehyde
b) furfural
c) crotonaldehyde
d) paraformaldehyde
e) chloral
f) butyraldehyde
g) acrolein

EXAMPLE 29

Example 3 is modified wherein a compound selected from the list below is reacted with the organic silicon-phosphorus chlorides and in the amount of about equal parts by weight thereby producing an organic silicon-phosphorus composition:
a) sodium polysulfide
b) propylene glycol
c) acetoaldehyde
d) fumaric acid
e) maleic anhydride
f) melamine
g) acrylic acid
h) aniline
i) phenol
j) furfuryl alcohol
k) diethylenetriamine
l) vinyl acetate
m) allyl alcohol
n) glycerol o) methyl magnesium chloride
p) epichlorohydrin
q) propylene oxide
r) polyepoxy resin
s) acetylene
t) isoprene with a free radical initiator
u) phosphoric acid
v) water
w) cellulose
x) glycine
y) mixtures of the above.

EXAMPLE 30

Example 1A is modified wherein hydrogen chloride is used in place of chlorine.

EXAMPLE 31

Example 30 is modified wherein an excess amount of an organic compound selected from the list below is mixed and reacted with the reaction product of Example 30 thereby producing an organic silicon-phosphorus composition. The mixtures is reacted for 6–12 hours:
a) methanol
b) allyl alcohol
c) ethyl glycol
d) acetic acid
e) oxalic acid
f) maleic acid
g) ethylene amine
h) propylene diamine
i) urea
j) melamine
k) furfural
l) acetoaldehyde
m) methyl magnesium chloride
n) tolylene 2,4-diisocyanate
o) epibromohydrin
p) propylene oxide
q) lignin
r) diethylene glycol
s) paraformaldehyde
t) acrylic acid
u) cellulose powder
v) polyvinyl alcohol
w) cotton seed oil
x) soy bean oil
y) phthalic anhydride
z) mixtures of the above.

EXAMPLE 32

About equal amounts of powdered silicon and phosphorus are mixed and a copper catalyst is added then heated to just below the boiling point of phosphorus in a closed container; then an excess amount of methyl chloride is passed thru the hot powdered mixture thereby producing a mixture of dimethyl dichlorosilane, dimethyl phosphorus chlorides, and other silicon-phosphorus containing compounds.

EXAMPLE 33

Example 32 is modified wherein the reaction products are slowly added to an excess amount of methanol in a cooled container while agitating thereby producing a mixture of organic silicon compounds, organic phosphorus compounds and organic silicon-phosphorus compounds.

EXAMPLE 34

Example 32 is modified wherein the reaction product are hydrolyzed by mixing with a large excess of water thereby producing a mixture of organic silicon compounds, organic phosphorus compounds and organic-silicon-phosphorus compounds.

EXAMPLE 35

About 10 parts by weight of 1A is mixed with an excess of water thereby producing a mixture of silica, polysilicic acid, phosphoric acid and silicon-phosphorus acids.

EXAMPLE 36

Example 35 is modified wherein an aqueous solution of sodium hydroxide is added in place of the water thereby producing sodium silicate, sodium phosphate and sodium silicon-phosphorus compounds.

EXAMPLE 37

About 10 mols of silicon dioxide powder, 10 mols of phosphorus powder and 20 mols of carbon powder are mixed and heated to just below the boiling temperature of the reactants in a closed container (electric furnace) and the carbon monoxide is allowed to escape thereby producing a mixture of Si, P and Si-P condensates; Then an excess amount of halide is passed thru the hot mixture thereby producing a mixture of silicon tetrahalide, silicon-phosphorus halide and phosphorus trihalide and some phosphorus pentahalide.

EXAMPLE 38

Example 1A is modified by adding one mol of water for one mol of halide while agitating and utilized in Example 2 in place of 1A.

EXAMPLE 39

Example 1B is modified wherein about one mol of water for each mol of phosphorus trihalide is added to the mixture while agitating and used in Example 2 in place of 1A.

EXAMPLE 40

Example 1B is modified wherein about one mol of phosphorus pentaoxide to 6 mols of phosphorus trihalide is added to the mixture while agitating and used in Example 2 in place of 1A.

EXAMPLE 41

Example 37 is modified wherein a metal is used in place of carbon and selected from the list below:
a) magnesium
b) zinc Other modifications of my invention will occur to those skilled in the art upon reading my disclosure. These are intended to be included within the scope of my invention as defined the appended claims.

I claim:

1. An organic silicon-phosphorus halides compound prepared by the process steps of:
   1. mixing and reacting the following components;
      A. silicon tetrachloride, 1 to 100 parts by weight
      B. phosphorus trichloride, 1 to 100 parts by weight
      C. an organic halide compound which is reacted with magnesium to form a Grignard reagent, in the amount wherein there are halogen atoms left on the silicon and/or phosphorus radicals, utilizing up to 300 parts by weight.

2. An organic silicon-phosphorus compound prepared by the process steps of:
   1. mixing the following components;
      A. silicon tetrachloride, in an amount of 1 to 100 parts by weight;
      B. phosphorus trichloride, in an amount of 1 to 100 parts by weight;
   2. admixing and reacting the following component;
      C. magnesium alkyl chloride, in an amount of up to 300 parts by weight.

* * * * *